United States Patent [19]

Byrne et al.

[11] Patent Number: 5,945,317
[45] Date of Patent: Aug. 31, 1999

[54] ANTIPARASITIC AGENTS

[75] Inventors: Kevin M. Byrne, W. Trenton; Arlene M. Dahl, North Brunswick; Anne Dombrowski, East Brunswick; Joyce A. Greene, Clark; John G. Ondeyka, Fanwood; Dan A. Ostlind, Watchung; Sheo Bux Singh, Edison; Diane M. Vesey, Woodbridge, all of N.J.

[73] Assignee: Merck & Co., Inc., Rahway, N.J.

[21] Appl. No.: 09/157,862

[22] Filed: Sep. 21, 1998

Related U.S. Application Data

[62] Division of application No. 08/914,998, Aug. 20, 1997, Pat. No. 5,834,260
[60] Provisional application No. 60/024,911, Aug. 30, 1996.
[51] Int. Cl.⁶ ...................... C07D 209/62; C07D 491/62; C07D 491/052; C12P 17/16
[52] U.S. Cl. ...................... 435/118; 435/254.1; 435/911; 548/417; 548/418
[58] Field of Search ................... 435/118, 254.1, 435/911; 548/417, 418

[56] References Cited

U.S. PATENT DOCUMENTS 5,399,582  3/1995  Dombrowski et al. .
5,492,902  2/1996  Belofsky et al. .

FOREIGN PATENT DOCUMENTS

WO 96/29073  9/1996  WIPO .

*Primary Examiner*—Johann Richter
*Assistant Examiner*—Taofiq A. Solola
*Attorney, Agent, or Firm*—Mollie M. Yang; David L. Rose

[57] ABSTRACT

Novel compounds isolated from the fermentation of producing cultures of Nodulisporium sp. are antiparasitic and insecticidal agents.

1 Claim, No Drawings

ANTIPARASITIC AGENTS

CROSS REFERENCE TO RELATED APPLICATIONS

This is a division of application Ser. No. 08/914,998 filed Aug. 20, 1997 now U.S. Pat. No. 5,834,260 which claims the benefit provisional application No. 60/024,911 filed Aug. 30, 1996.

BACKGROUND OF THE INVENTION

U.S. Pat. No. 5,399,582 describes novel antiparasitic compounds having the structural formulae:

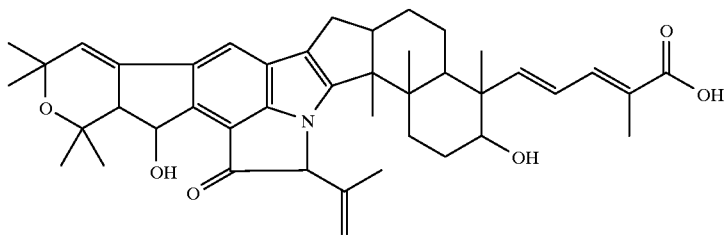

Compound 1

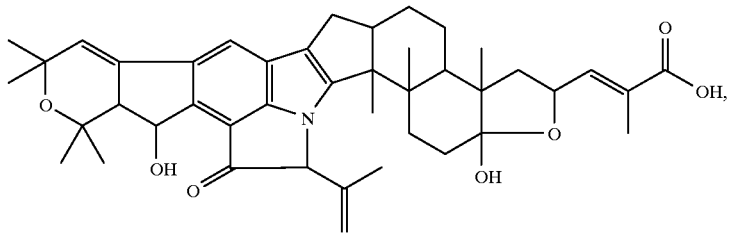

Compound 2 and

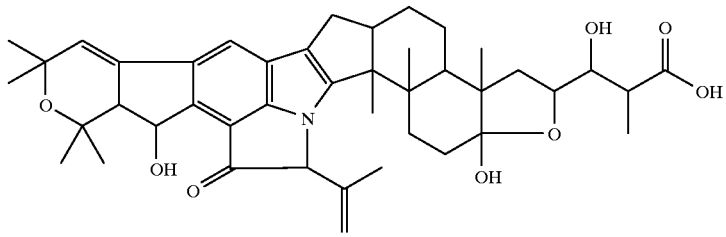

Compound 3

The above compounds are isolated from the fermentation medium of Nodulisporium sp., ATCC 74245, and are potent ectoparasiticidal, antiparasitic, and insecticidal agents.

SUMMARY OF THE INVENTION

The instant invention is concerned with novel antiparasitic agents and ectoparasiticidal agents. Thus it is an object of this invention to disclose such novel compounds. A further object is to provide a novel method for the preparation of such compounds. A further object is to describe the microorganism used to prepare such compounds and the fermentation conditions applicable to such production. A still further object is to describe compositions and methods using the instant compounds as antiparasitic agents. Further objects will become apparent from reading the following description.

DETAILED DESCRIPTION OF THE INVENTION

The present invention provides novel compounds having the following structures, and their pharmaceutically acceptable salts and esters:

Compound 4
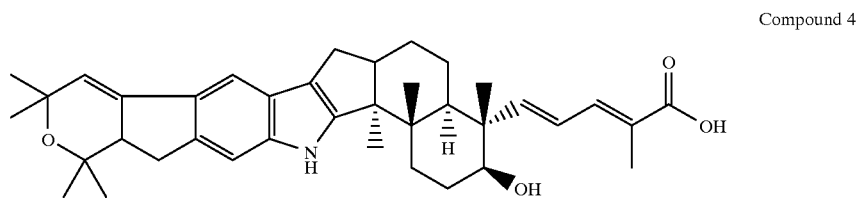
Compound 5
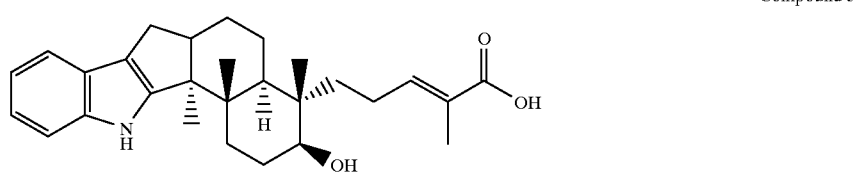
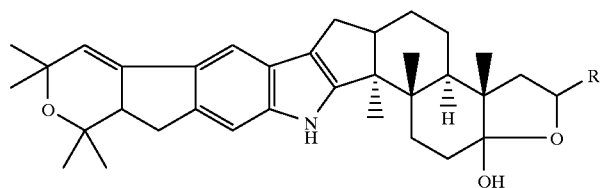
Compound 6:
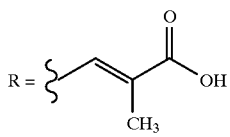
Compound 7:
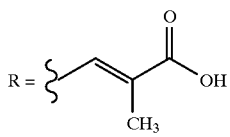
Compound 8
Compound 12
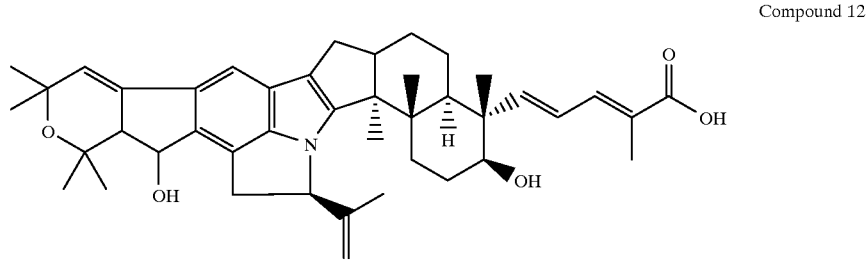

-continued
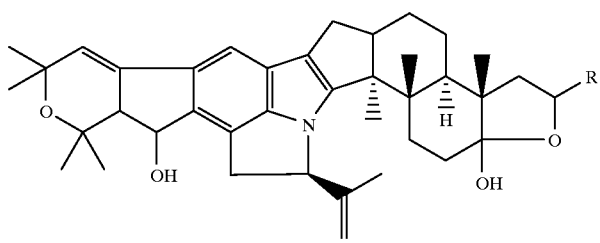
Compound 13
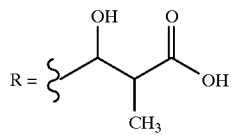
Compound 14
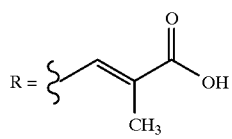
Compound 15
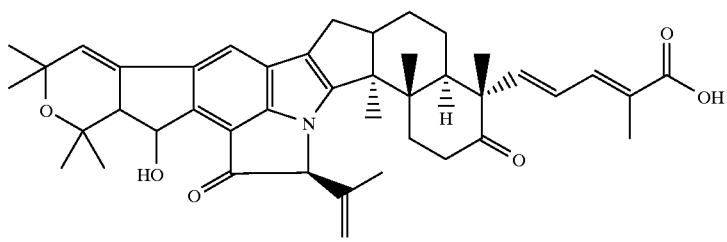
Compound 16
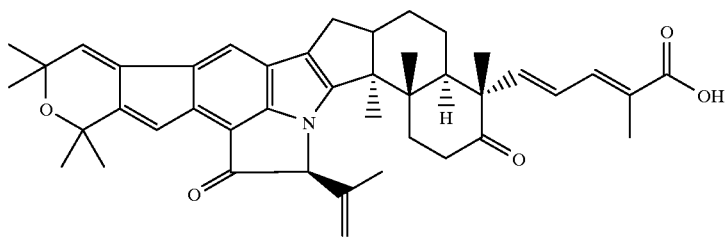
Compound 17
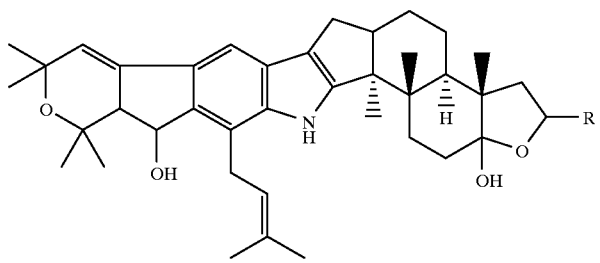
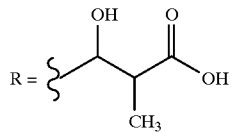

-continued

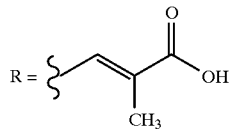

Compound 18

The above structural formulae are shown without a definitive stereochemistry at certain positions and with a defined stereochemistry at other positions and the instant invention should be construed as encompassing all such stereoisomers. In particular, the stereoisomers at the various asymmetric centers may be oriented either α- or β- representing such groups being below or above the general plane of the molecule, respectively.

The novel compounds of the instant invention are structurally related to compounds 1, 2 and 3, and are prepared by the fermentation of a strain of the fungal genus Nodulisporium, designated MF5954 in the culture collection of Merck & Co., Inc., Rahway, N.J., or mutants derived therefrom. MF5954 has been deposited in the permanent collection of the American Type Culture Collection at 12301 Parklawn Drive, Rockville, Md. 20852, and has been given the accession number 74245. The deposit was made on Sep. 21, 1993 under The Budapest Treaty on the International Recognition of the Deposit of Microorganisms for the Purposes of Patent Procedure. The morphological and cultural characteristics of Nodulisporium sp. MF5954 are described in U.S. Pat. No. 5,399,582.

Mutants derived from ATCC 74245 have been shown to produce novel compounds of the present invention. Although mutation may be induced by several techniques generally known in the art such as exposure to chemical mutagen, gamma radiation, ultraviolet irradiation, and the like, the particular mutants of the instant invention are produced by exposure to a chemical mutagen, specifically N-methyl-N'-nitro-N-nitrosoguanidine (NTG). Thus, wild-type MF5954 (ATCC 74245) or a mutant derived therefrom is treated with NTG at a concentration ranging from about 10 to about 2000 μg/mL and the culture is incubated at the preferred growth temperature. Aliquots of the culture are removed at different times after exposure, and plated on agar for growth, either directly or after being grown first in a liquid medium. Survivors of the NTG treatment are randomly selected and fermented, and the fermentation broth is periodically checked for production of compounds that are structurally related to compounds 1–3 using reversed phase high performance liquid chromatography with UV detection at 270 nm. Cultures that appear to produce novel compounds that are structurally related to compounds 1, 2 and 3 are fermented in larger scale to allow isolation of sufficient amount for structure determination.

NTG treatment of wild-type MF5954 or a mutant whose lineage can be traced back to MF5954 provided the following mutant cultures identified by the Merck culture collection numbers. Each of the mutant cultures has been deposited in the permanent collection of the American Type Culture Collection at 12301 Parklawn Drive, Rockville, Md. 20852, and has been assigned the accession number as indicated below. The deposits were made on Aug. 8, 1996 under The Budapest Treaty on the International Recognition of the Deposit of Microorganisms for the Purposes of Patent Procedure. The characteristics of the mutants are described in the Examples section.

| Merck No. | ATCC No. |
|---|---|
| MF6047 | 74380 |
| MF6087 | 74381 |
| MF6206 | 74382 |
| MF6222 | 74383 |

In another aspect the present invention provides a process for the preparation of a compound selected form Compounds 4, 5, 6, 7, 8, 12, 13, 14, 15, 16, 17 and 18 which comprises fermenting a strain of Nodulisporium sp. capable of producing said compound in a medium containing assimilable sources of carbon, nitrogen and trace element, and isolating said compound.

The instant compounds are produced during the aerobic fermentation of suitable solid or aqueous nutrient media under conditions described hereinafter, with a producing strain of Nodulisporium sp. Aqueous and solid media such as those used for the production of many antibiotic substances are suitable for use in the process for the production of these polycyclic compounds.

Such nutrient media contain sources of carbon and nitrogen assimilable by the microorganism, and generally low levels of inorganic salts. In addition, the fermentation media may contain traces of metals necessary for the growth of the microorganisms, and production of the desired compounds. These are usually present in sufficient concentrations in the complex sources of carbon and nitrogen, which may be used as nutrient sources, but can, of course, be added separately to the medium if desired.

In general, carbohydrates such as sugars, for example glucose, sucrose, maltose, lactose, dextrin, cerelose, corn meal, oat flour, and the like, and starches are suitable sources of assimilable carbon in the nutrient media. Other carbon sources include polyhydroxy alcohols such as mannitiol, sorbitol, or glycerol and organic acids such as succinic acid, citric acid, lactic acid, and propionic acid. The exact quantity of the carbon source which is utilized in the medium will depend, in part, upon the other ingredients in the medium, but it is usually found that an amount of carbohydrate between 1 and 150 g/L in the medium is satisfactory. These carbon sources can be used individually or several such carbon sources may be combined in the same medium.

Various nitrogen sources such as nitrate or ammonium salts, amino acids, protein hydrolysates, yeast hydrolysates, yeast autolysates, yeast cells, tomato paste, corn meal, oat flour, soybean meal, casein hydrolysates, yeast extracts, corn steep liquors, distillers solubles, cottonseed meal, meat extract and the like, are readily assimilable by Nodulisporium sp. in the production of the instant compounds. The various sources of nitrogen can be used alone or in combination, each in amounts ranging from 1 to 20 g/L in the medium.

Among the nutrient inorganic salts which can be incorporated in the culture media are the customary salts capable of yielding sodium, potassium, magnesium, ammonium, calcium, phosphate, sulfate, chloride, carbonate, and like ions. Also included are trace metals such as iron, zinc, manganese, copper, boron, molybdenum and the like.

The fermentation employing Nodulisporium sp. can be conducted at temperatures ranging from about 20° C. to about 40° C. For optimum results, it is most convenient to conduct these fermentations at a temperature in the range of from about 22° C. to about 36° C. Temperatures of from about 22° C. to about 30° C. are most preferred. The pH of the nutrient medium suitable for producing the instant compounds can vary from about 4.0 to about 8.0 with a preferred range of from about 5.5 to about 7.3. It has also been found that production of the present compounds is favored in the absence of light.

Small scale fermentations are conveniently carried out by placing suitable quantities of the nutrient medium in a flask employing known sterile techniques, inoculating the medium with vegetative cellular growth of Nodulisporium sp., loosely stoppering the flask with cotton and permitting the fermentation to proceed in a constant room temperature of about 22° C. to about 30° C. on a rotary shaker at from 95 to 300 rpm for about 7 to 35 days. For larger scale work, it is preferable to conduct the fermentation in suitable tanks provided with an agitator and a means of aerating the fermentation medium. The nutrient medium is made up in the tank and, after sterilization, is inoculated with a source of vegetative cellular growth of Nodulisporium sp. The fermentation is allowed to continue for from 7 to 30 days while agitating and/or aerating the nutrient medium at a temperature in the range of from about 22° C. to 30° C. The degree of aeration is dependent upon several factors such as the size of the fermentor, agitation speed, and the like. Generally the larger scale fermentations are agitated at about 95 to 300 rpm and/or treated with about 50 to 500 liters per minute (LPM) of air.

The separation of the instant compounds from the whole fermentation broth and the recovery of the compound is carried out by solvent extraction and application of chromatographic fractionations with various chromatographic techniques and solvent systems.

The instant compounds have slight solubility in water, but are soluble in organic solvents. This property conveniently may be employed to recover the compound from the fermentation broth. Thus, in one recovery method, the whole fermentation broth is combined with approximately an equal volume of an organic solvent. While any organic solvent may be employed, it is preferable to use a water immiscible solvent such as ethyl acetate, methylene chloride, methyl ethyl ketone, chloroform and the like in the first extraction. Generally several extractions using the same or different solvents are desirable to achieve maximum recovery. The solvent removes the instant compounds as well as other substances lacking the antiparasitic activity of the instant compound. If the solvent is a water immiscible one, the layers are separated and the organic solvent is concentrated under reduced pressure. The residue is placed onto a chromatography column preferably containing silica gel. The column retains the desired product and some impurities, but lets many of the impurities, particularly the nonpolar impurities, pass through. The column is washed with organic solvents or a combination thereof of increasing polarity to effect separation of the desired compounds. The solvent is evaporated and the residue further chromatographed using column chromatography, thin layer chromatography, preparative thin layer chromatography, high pressure liquid chromatography and the like, with silica gel, aluminum oxide, ion exchange resins, dextran gels and the like, as the chromatographic medium, with various solvents and combinations of solvents as the eluent. Thin layer, high pressure, liquid and preparative layer chromatography may be employed to detect the presence of, and to isolate the instant compounds.

The use of the foregoing techniques as well as others known to those skilled in the art will afford purified fractions containing the instant compounds. The presence of the desired compound is determined by analyzing the various chromatographic fractions for biological activity or physico-chemical characteristics. Structures of compounds have been determined by detailed analysis of the various spectral characteristics of the compounds, in particular their nuclear magnetic resonance, mass, ultraviolet and infrared spectra.

Compounds of the present invention possess a carboxylic acid moiety and are therefore capable of forming pharmaceutically acceptable salts with bases. The term "pharmaceutical" includes both human and veterinary medicaments. The term "pharmaceutically acceptable salts" refers to salts prepared from pharmaceutically acceptable non-toxic bases including inorganic bases and organic bases. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

The acids of the present invention may be converted to the corresponding esters using methods well known in the art. The isolated and purified acids may be used as the starting material; alternatively, the fermentation extract, or fractions of varying purity, is directed treated with an esterifying agent to convert the acids into their corresponding esters. For example addition of trimethylsilyldiazomethane to the fermentation extract provides the corresponding methyl ester, and the resulting ester is then isolated from the fermentation extract. The ester thus isolated may of course be hydrolyzed to the parent acid if desired.

The compounds of this invention find their primary use as antiparasitic agents in the treatment and/or prevention and treatment of diseases caused by parasites, for example, arthropod parasites such as ticks, lice, fleas, and other biting insects in domesticated animals and poultry, such as Tenophalides, Ixodes, Psoroptes, Lucilia and Hemotobia. They are also effective in the treatment or prevention of parasitic diseases, such as helminthiasis, that occur in other animals including humans. The optimum amount to be employed for best results will, of course, depend upon the species of animal to be treated and the type and severity of parasitic infection or infestation. Generally, good results are obtained with the novel compounds by the oral administration of from about 0.001 to about 100 mg per kg of animal body weight, such total dose being given at one time or in divided doses over a relatively short period of time such as 1–5 days. With the novel compound of the present invention, excellent control of such parasites is obtained in animals by administering from about 0.025 to about 50 mg per kg of body weight in a single dose. Repeat treatments are given where required to combat re-infections and are dependent upon the species of parasite and the husbandry techniques being employed. The techniques for administering these materials to animals are known to those skilled in the veterinary field.

The instant compounds are also active against household pests such as the cockroach, Blatella sp., ants, Solenopsis clothes moth, Tineola sp., carpet beetle, Attagenus sp. and the housefly *Musca domestics.*

The compounds of the present invention are also useful against insect pests of stored grains such as Tribolium sp., Tenebrio sp. and of agricultural plants such as spider mites, (Tetranvchus sp.), aphids, Acyrthiosiphon migratory orthopterans such as locusts and immature stages of insects living on plant tissue. The compounds are useful as nematocides for the control of soil nematodes and plant parasites such as Meloidogyne sp. which may be of importance in agriculture.

The compounds of the present invention are preferably used in the form of a pharmaceutical composition, which comprises a compound of the present invention and a pharmaceutically acceptable carrier. As used herein, pharmaceutical composition includes medicaments for human and veterinary uses. The term "composition", as in pharmaceutical composition, is intended to encompass a product comprising the active ingredient(s), and the inert ingredient (s) that make up the carrier, as well as any product which results, directly or indirectly, from combination, complexation or aggregation of any two or more of the ingredients, or from dissociation of one or more of the ingredients, or from other types of reactions of one or more of the ingredients. Accordingly, the pharmaceutical compositions of the present invention encompass any composition made by admixing a compound of the present invention and a pharmaceutically acceptable carrier.

The compounds of the present invention can be administered orally in a unit dosage form such as a capsule, bolus or tablet, or as a liquid drench that is normally a solution, suspension or dispersion of the active ingredient usually in water together with a suspending agent such as bentonite and a wetting agent or like excipient. Generally, the drenches also contain an antifoaming agent. Drench formulations generally contain from about 0.001 to about 1.0% by weight of the active compounds. Preferred drench formulations may contain from about 0.01 to about 0.1% by weight. The capsules and boluses comprise the active ingredient admixed with a carrier vehicle such as starch, talc, magnesium stearate, or dicalcium phosphate.

Where it is desired to administer the compounds of the present invention in a dry, solid unit dosage form, capsules, boluses or tablets containing the desired amount of the instant compounds usually are employed. These dosage forms are prepared by intimately and uniformly mixing the active ingredient with suitable finely divided diluents, fillers, disintegrating agents and/or binders such as starch, lactose, talc, magnesium stearate, vegetable gums and the like. Such unit dosage formulations may be varied widely with respect to their total weight and content of the antiparasitic agent depending upon factors such as the type of host animal to be treated, the severity and type of infection and the weight of the host.

When the compounds of the present invention are to be administered via an animal feedstuff, they are intimately dispersed in the feed or used as a top dressing or in the form of pellets which may then be added to the finished feed or optionally fed separately. Alternatively, the antiparasitic compounds of our invention may be administered to animals parenterally, for example, by intraruminal, intramuscular, intratracheal, or subcutaneous injection in which event the active ingredient is dissolved or dispersed in a liquid carrier vehicle. For parenteral administration, the active material is suitably admixed with an acceptable vehicle, preferably of the vegetable oil variety such as peanut oil, cotton seed oil and the like. Other parenteral vehicles such as organic preparation using solketal, glycerol, formal and aqueous parenteral formulations are also used. The compounds of the present invention are dissolved or suspended in the parenteral formulation for administration; such formulations generally contain from about 0.55% to about 5% by weight of the instant compound.

When the compounds described herein are administered as components of the feed of the animals, or dissolved or suspended in the drinking water, compositions are provided in which the active compounds are intimately dispersed in an inert carrier or diluent. By inert carrier is meant one that will not react with the antiparasitic agent and one that may be administered safely to animals. Preferably, a carrier for feed administration is one that is, or may be, an ingredient of the animal ration.

Suitable compositions include feed premixes or supplements in which the instant compounds are present in relatively large amounts and which are suitable for direct feeding to the animal or for addition to the feed either directly or after an intermediate dilution or blending step. Typical carriers or diluents suitable for such compositions include, for example, distillers' dried grains, corn meal, citrus meal, fermentation residues, ground oyster shells, wheat shorts, molasses solubles, corn cob meal, edible bean mill feed, soy grits, crushed limestone and the like. The compounds of the present invention are intimately dispersed throughout the carrier by methods such as grinding, stirring, milling or tumbling. Compositions containing from about 0.005% to about 2.0% by weight of the instant compound are particularly suitable as feed premixes. Feed supplements, which are fed directly to the animal, contain from about 0.0002% to about 0.3% by weight of the instant compound.

Such supplements are added to the animal feed in an amount to give the finished feed the concentration of active compound desired for the treatment and control of parasitic diseases. Although the desired concentration of the compounds of the present invention will vary depending upon the factors previously mentioned as well as upon the particular compound employed, the compounds of this invention are usually fed at concentrations of between about 0.001% to about 0.2% in the feed in order to achieve the desired antiparasitic result.

In addition, where the compound is to be added to an animal's feed, it is possible to utilize the dried mycelial cake from the fermentation broth. The mycelia contain a preponderance of the activity and since the level of the activity of the mycelia can be determined, it can be added directly to the animal's feed.

The compounds of this invention also are useful in combating agricultural pests that inflict damage upon crops while they are growing or while in storage. The compounds are applied using known techniques as sprays, dusts, emulsions and the like, to the growing or stored crops to effect protection from such agricultural pests.

Compounds of this invention may be co-administered with anthelmintic agents. These anthelmintic agents are meant to include, but not be restricted to, compounds selected from the avermectin and milbemycin class of compounds such as ivermectin, avermectin, abamectin, emamectin, eprinamectin, doramectin, fulladectin, moxidectin, Interceptor and nemadectin. Additional anthelmintic agents include the benzimidazoles such as thiabendazole, cambendazole, parbendazole, oxibendazole, mebendazole, flubendazole, fenbendazole, oxfendazole, albendazole, cyclobendazole, febantel, thiophanate and the like. Additional anthelmintic agents include imidazothiazoles and tetrahydropyrimidines such as tetramisole-levamisole, butamisole, pyrantel, pamoate, aoxantel or morantel.

Compounds of this invention may be co-administered with fipronil.

Compounds of this invention may be co-administered with an insect growth regulator with molt inhibiting activity such as lufenuron and the like.

Compounds of this invention may be co-administered with ecdysone agonist such as tebufenozide and the like, which induces premature molt and causes feeding to cease.

The co-administered compounds are given via routes, and in doses, that are customarily used for those compounds.

Also included in the present invention are pharmaceutical compositions containing a compound of the present invention in combination with an anthelmintic agent, fipronil, an insect growth regulator, or a ecdysone agonist.

The antiparasitic activity of the instant compounds may be determined by orally administering via the feed, a sample of the individual compound, a mixture of such compounds, a concentrated extract, and the like to a mouse which had been infected 3 days earlier with an appropriate parasite. At 11, 12 and 13 days after the initiation of the medication, the feces of the mouse are examined for eggs, and on the next day the mouse is sacrificed and the number of worms present in the proximal portion of the small intestine are determined. Activity is observed when there is a significant reduction of egg and worm counts when compared to infected, unmedicated controls.

Some compounds of the present invention, in particular compounds 12, 13 and 14, may also be used as intermediates or precursors for the preparation of compounds 1, 2 and 3. Thus compounds 12, 13 and 14 may be converted to compound 1, 3 and 2, respectively, using conventional benzylic oxidation methodologies, or by feeding the former to a strain of Nodulisporium sp. capable of converting them to the latter, such as MF5954.

In the following examples, the media used have the following compositions:

TABLE 1

| Ingredients (g/L) | Seed Media | |
|---|---|---|
| | SM1 | SM2 |
| Glucose | 10 | 10 |
| Oat Flour | 10 | 10 |
| Corn Steep Liquor | 5 | — |
| Corn Steep Powder* | — | 2.5 |
| Tomato Paste** | 40 | 40 |
| $FeSO_4.7H_2O$ | 10 (mg) | 10 (mg) |
| $MnSO_4.H_2O$ | 10 (mg) | 10 (mg) |
| $ZnSO_4.7H_2O$ | 2 (mg) | 2 (mg) |
| $CaCl_2$ | 1 (mg) | 1 (mg) |
| $H_3BO_3$ | 0.56 (mg) | 0.56 (mg) |
| $CuCl_2.2H_2O$ | 0.25 (mg) | 0.25 (mg) |
| $(NH_4)_6Mo_7O_{24}.4H_2O$ | 0.19 (mg) | 0.19 (mg) |

*Marcor
**Contadina

Adjust pH to 6.8 before autoclaving.

TABLE 2

| Ingredients (g/L) | Production Media | | |
|---|---|---|---|
| | PM1 | PM2 | PM3 |
| Glucose | 60 | 70 | 82 |
| Glycerol | 60 | 100 | 80 |
| $NH_4Cl$ | 3 | 3 | 5 |
| Glutamate (MSG) | 10 | 10 | 14 |
| Amicase* | — | 8 | — |
| L-Tryptophan | 0.7 | 0.7 | 0.3 |
| $K_2HPO_4$ | 1 | 1 | 1 |
| $CaCO_3$ | 1 | 1 | 1 |
| $MgSO_4.7H_2O$ | 0.5 | 0.5 | 0.5 |
| MES Buffer** | 20 | 20 | 20 |
| $FeSO_4.7H_2O$ | 10 (mg) | 10 (mg) | 10 (mg) |
| $ZnSO_4.7H_2O$ | 10 (mg) | 10 (mg) | 10 (mg) |
| $MnSO_4.H_2O$ | 2 (mg) | 2 (mg) | 2 (mg) |
| $CuSO_4.5H_2O$ | 1 (mg) | 1 (mg) | 1 (mg) |
| $CoCl_2.6H_2O$ | 0.8 (mg) | 0.8 (mg) | 0.8 (mg) |

*Quest International
**2-[N-Morpholino]ethanesulfonic acid

Adjust pH to 6.0 before autoclaving.

EXAMPLE 1

General Procedure for the Fermentation Production of Compounds of the Present Invention Fermentation productions of compounds of the present invention in flasks and/or tubes are carried out according to the following procedures. All flask fermentations are carried out in the dark.

Seed Culture

A 50 mL portion of the Seed Medium in non-baffled 250 mL Erlenmeyer flasks is inoculated with 1–2 mL of a mycelial suspension (such as one that had been frozen in glycerol) of Nodulisporium sp. and the culture is incubated with shaking at 220 rpm for 2 days at 29° C. Alternatively, 10 mL of Seed Medium in 50 mL Erlenmeyer flasks is inoculated with colony plugs (crushed) and incubated at 220 rpm for 3 days at 29° C., and the resulting seed culture used to inoculate the production medium.

Production Culture

A 50 mL portion of production medium is inoculated with 2 mL of a seed culture, and the resulting culture is incubated with shaking at 220 rpm for 14–21 days at 29° C. The pH of a 2.0 mL aliquot from shake flasks is adjusted to <7.0 with 6N HCl, 10 mL of methanol added in a 15-mL polypropylene centrifuge tube. The mixture is shaken for 30 minutes, centrifuged to remove large particulates, and the extract filtered into an HPLC vial. Compounds of the present invention are quantified by reversed phase chromatography, preferably on a Waters C-18 Symmetry Column (4.6 mm ID×100 mm column length, 3.5 μm particle size). The column is eluted isocratically with a mobile phase consisting of HPLC-grade water containing 0.1% trifluoroacetic acid/acetonitrile (35:65) at 50° C. and a flow rate of 0.9 mL/min. The absorbance of the eluate is monitored at 270 nm.

EXAMPLE 2

Fermentation Production of Compounds 4 and 5

Inoculum was grown at 25° C. in three sequential seed stages using culture MF5954 (ATCC 74245) and seed medium of the following composition per liter: yeast extract, 4 g; malt extract, 8 g; glucose, 8 g. The production fermentation was run either in an 800 L or a 1,900 L vessel containing production medium of the following composition per liter: glycerol, 40 g; glucose, 20 g; yeast extract, 5 g; soybean meal, 5 g; tomato paste, 5 g; trisodium citrate, 2 g; ammonium sulfate, 2 g. The inoculum volume was 3–4% of the final medium volume. The fermentation was run at 25° C., with the pressure, airflow and agitator speed adjusted to maintain a minimum dissolved oxygen concentration of 50% of atmospheric saturation. Glycerol was added intermittently to sustain the fermentation for 640 hours, after which the batch was harvested for isolation of the desired compounds.

EXAMPLE 3

Fermentation Production of Compounds 6 and 7

Inoculum was grown at 25° C. in three sequential seed stages using culture MF 6047 (ATCC 74380) and seed medium SM1. The production fermentation was run in a 1,900 L vessel, containing production medium PM1. The inoculum volume was 3–4% of the final medium volume. The fermentation was run at 25° C., with the pressure, airflow and agitator speed adjusted to maintain a minimum dissolved oxygen concentration of 50% of atmospheric saturation. Each batch was harvested for isolation of the desired compounds after 550–600 hours.

EXAMPLE 4

Fermentation Production of Compounds 8, 17 and 18

Seed Culture

A 10 mL portion of SM2 Medium in non-baffled 50 mL Erlenmeyer flasks was inoculated with a colony plug (crushed) of culture MF6222 (ATCC 74383), and the culture was incubated with shaking at 220 rpm for 4 days at 29° C.

Production Culture

A 10 mL portion of PM3 production medium was inoculated with 0.6 mL of a seed culture, and the resulting culture was incubated with shaking at 220 rpm for 14–15 days at 29° C. A 2.0 mL aliquot from the shake flask was extracted and the extract analyzed by HPLC using the procedure described in Example 1. Compound 8 was observed at a retention time of 7.8 minutes. A peak was observed at a retention time of 6.8, compound 18. Another peak was observed at a retention time of 11.2, compound 17.

To obtain sufficient quantity of compounds 17 and 18 for structure determination, 2 L (40 flasks) of production medium were prepared as follows: A 50 mL portion of SM2 Seed Medium in non-baffled 250 mL Erlenmeyer flasks was inoculated with 1–2 mL of a mycelial suspension (preserved with 10% glycerol and frozen at −85° C.) of culture MF6222 (ATCC 74383). The culture was incubated with shaking at 220 rpm for 3 days at 29° C. A 50 mL portion of PM2 production medium was inoculated with 1 mL of seed culture, and the resulting culture was incubated with shaking at 220 rpm for 22 days at 29° C. The flask contents were pooled yielding 1.8 L and extracted with methylethylketone.

EXAMPLE 5

Fermentation Production of Compounds 12, 13 and 14

Seed Culture

A crushed agar plug bearing a colony of MF6206 (ATCC 74382) was used to inoculate a 10-ml, portion of SM1 Seed Medium in a non-baffled 50-mL Erlenmeyer flask. The culture was incubated with shaking at 220 rpm for 3 days at 29° C.

Production Culture

A 50-mL portion of PM1 Production Medium was inoculated with 2 mL of the seed culture, and the resulting culture was incubated with shaking at 220 rpm for 15 days at 29° C. in darkness. A 10-mL volume of methanol was added to a 2-mL portion of the fermentation, and the mixture was shaken for 30 minutes. Following centrifugation to remove large particles, the extract was filtered into HPLC vials.

The HPLC assay was done on a Zorbax SB-C8 reversed phase column (3 mm ×25 mm). The column was eluted isocratically with a mobile phase consisting of water containing 0.1% trifluoroacetic acid/acetonitrile (42:58) at 50° C. and a flow rate of 1.0 mL/min. The absorbance of the eluate was monitored at 270 nm. The retention times of the compounds made by MF6206 (ATCC 74382) are slightly shorter than those of the compounds made by the parental culture. Examination of their spectra revealed that they were not compounds 1, 2 or 3; each peak lacked the characteristic absorption at 400 nm.

To obtain sufficient quantities of the new compounds for structure determination, 2 L (40 flasks) of PM3 Production Medium was inoculated as described in the fermentation procedure. In this case the SM1 Seed Medium was inoculated with 2-mL of a mycelial suspension that had been preserved by freezing in 10% glycerol at −70 ° C. The production fermentation was harvested at 21 days.

EXAMPLE 6

Fermentation Production of Compound 15

Seed Culture

A 50 mL portion of SM1 Seed Medium in a non-baffled 250 mL Erlenmeyer flask was inoculated with 1–2 mL of a mycelial suspension (preserved with 10% glycerol and frozen at −85 ° C.) of culture MF6087 (ATCC 74381). The culture was incubated with shaking at 220 rpm for 2 days at 25° C.

Production Culture

Forty flasks each containing 50 mL of PM1 production medium were each inoculated with 2 mL of the seed culture, and the resulting culture was incubated with shaking at 220 rpm for 30 days at 29° C. The appearance of compound 15 was confirmed by HPLC on a Zorbax SB-C8 reversed phase column eluted isocratically with a mobile phase consisting of HPLC-grade water containing 0.1% trifluoroacetic acid/ acetonitrile (46:54) at 50° C. and a flow rate of 1.0 mL/min. The absorbance of the eluate was monitored at 270 nm. The flask contents were pooled yielding 1.5 L and extracted with methlyethylketone.

Compound 15 was observed as a shoulder on compound 2. Retention times were 17.4 minutes for compound 2 versus 18.3 minutes for compound 15.

EXAMPLE 7

Purification and Preliminary Characterization of Compounds 4 and 5

Extract from large scale fermentation of MF5954 was dewatered, extracted with isopropyl alcohol and passed through an SP-207 column (Tosohaus). The material was eluted with methanol and partitioned with hexane. The methanol solution was concentrated, redissolved in methylene chloride and charged to a silica gel column (70 L) and eluted with isopropyl acetate followed by 10%, 20%, 30%, 50% and 100% methanol in isopropyl acetate (1 col. vol. each). A portion of the 50% methanol fraction was taken to dryness and found to contain a large peak at 270 nm (HPLC)

which could be related to the previously isolated compounds 1, 2 and 3 (U.S. Pat. No. 5,399,582). This material was fractionated through a 2-L Sephadex LH20 funnel twice, concentrated and charged to a 2.5-L silica gel column and eluted with 70-30-1: methylene chloride-acetone-0.2% acetic acid. Cuts 13–18 (400 mL each) contained the desired compound. These cuts were dried, redissolved in methylene chloride and a portion charged to a semipreparative HPLC column (Zorbax RX-C8 (9.6 by 250 mm)) at room temperature monitored at 270 nm with a flow rate of 8 mL/min. The solvent system used was 65-35 acetonitrile-water with 0.1% TFA and the compound was found in cuts 17–19. This was the final chromatographic step used for purification to yield 3 mg of compound 4. The UV max was at 270 nm only and did not resemble the uv spectra of compounds 1–3.

A later fraction from the Sephadex LH20 step above was rechromatographed on a 1-L LH20 column and fractions 52 to 56 contained compound 5 (5 mg). Purity was determined by analytical HPLC (Zorbax RX C-8 4.6 by 250 mm) column at 40° C. monitored at 270 nm. The solvent system was 72-28 acetonitrile-water with 0.1% TFA at a flow rate of 1 mL/min. The UV maximum was 225 nm. Both compounds 4 and 5 were characterized as analogs of compounds 1–3 by NMR and MS studies.

Mass spectra were recorded on Jeol SX-102A (electron impact, EI,90eV) and JEOL HX110 (Fast Atom Bombardment, FAB) and TSQ70B (LC-MS-ESI, Liquid chromatography-Electrospray ionization) mass spectrometers. Exact mass measurements were performed at high resolution (HR-EI) using perfluorokerosene (PFK) as an internal standard. The FAB spectrum was run in a matrix of dithiothreitol dithioerythritol (20/80). The exact mass measurements were made at high resolution with ultramark 1960 (Fomblin) as the reference compound. HR-ESI data was obtained on a Finnigan NewStar FTMS. Critical high resolution data is indicated below:

| Found | Calculated | Formula | Assignment |
|---|---|---|---|
| Compound 4 | | | |
| 583.3677 | 583.3661 | C38H49NO4 | M+ |
| Compound 5 | | | |
| 435.2751 | 435.2773 | C28H37NO3 | M+ |

$^{13}$C and $^1$H NMR Data $^{13}$C NMR data were recorded in $CD_2Cl_2$ at 75 and 100 MHz on Varian 300 and Varian Unity 400 NMR spectrometers, respectively, at 25° C. Chemical shifts are given in ppm relative to tetramethylsilane (TMS) at zero ppm using the solvent peak at 53.8 ppm as internal standard.

Compound 4 (100 MHz): 172.3, 155.26, 152.68, 143.67, 141.34, 140.67, 138.43, 132.68, 126.29, 126.2, 126.12, 118.96, 118.12, 110.17, 108.55, 77.90, 76.30, 74.37, 54.37, 50.30, 50.14, 48.0, 45.63, 40.04, 34.21, 33.63, 32.18, 30.52, 30.19, 28.31, 27.86, 26.41, 25.75, 22.60, 19.35, 14.74, 12.86, 11.9 ppm.

The carbon count is in agreement with the molecular formula $C_{38}H_{49}NO_4$ derived by HR MS.

Compound 5 (75 MHz): 172.15, 152.20, 144.0, 142.10, 128.90, 126.26, 120.70, 119.70, 118.71, 117.98, 112.63, 73.94, 54.33, 50.27, 42.57, 41.38, 40.43, 37.05, 33.75, 28.37, 28.29, 26.34, 24.05, 23.46, 19.45, 17.28, 14.90, 12.53 ppm.

The carbon count is in agreement with the molecular formula $C_{28}H_{39}NO_3$ derived by HR MS.

$^1$H NMR spectra were recorded on 300 or 400 MHz spectrometers. Chemical shifts are indicated in ppm relative to TMS at zero ppm using the solvent peaks as internal standards.

Compound 4 (400 MHz): δ0.99(3H,s), 1.06(3H,s), 1.08 (3H,s), 1.095(3H,s), 1.29(3H,s), 1.31(3H,s), 1.35(3H,s), 1.35(1H,m), 1.45(1H,m), 1.7(1H,m), 1.8(1H,m), 1.75 (1H, m), 1.80(2H,m), 1.55(1H,m), 1.70(1H,m), 1.92(3H, d J=1.6 Hz), 2.25(1H,dd J=110, 12.4 Hz), 2.59(1H,dd J=12.4, 16.0 Hz), 2.65(1H,dd J=7.2, 15.6 Hz), 2.85(1H,dq J=2.8, 7.6,9.2 Hz), 3.05(1H,dd J=9.2,16.4 Hz), 3.45(1H,m), 5.9(1H,d J=3.2 Hz), 5.91(1H,d J=15.2 Hz), 6.36(1H,dd J=11.2, 15.6 Hz), 7.14(1H,d J=0.8 Hz), 7.25(1H,d J=11.2 Hz), 7.37(1H,d J=0.8 Hz), Compound 5 (300 MHz): δ0.85(3H,s), 1.0(3H,s), 1.12 (3H,s), 1.3–1.7(11H,m), 1.85(3H,d J=0.8 Hz), 2.15(2H,m), 2.3(1H,dd J=10.8, 13.2 Hz), 2.6(1H,dd J=6.3,13.2 Hz), 2.8(1H,m), 3.52(1H,m), 6.8(1H,dd J=9.0,10.2 Hz), 6.92(1H, dq J=2.1,7.8,13.2 Hz), 6.95(1H,dq J=2.1,7.8,13.2 Hz), 7.27 (1H,d J=2.1 Hz), 7.29(1H,d J=2.1 Hz).

Abbreviations: s=singlet, d=doublet, q=quartet, br=broad, m=multiplet, J=$^1$H-$^1$H coupling constant in Hertz (±0.5 Hz, ~=approximately).

EXAMPLE 8

Purification and Characterization of Compounds 6 and 7

A large scale fermentation of MF6047 (ATCC 74380) was dewatered, extracted with isopropanol and passed through an SP-207 column. The captured material was eluted with methanol and partitioned with hexane. A small portion of the methanol extract was dried (4.6 G) and charged to a silica gel column (1 liter) and cuts 13–16 collected and dried (800 mg). This material was dissolved in methanol and charged to a Sephadex LH20 column (400 ml) in methanol and compounds of interest were found in cuts 71–76 (50 mg) as determined by TLC and HPLC as described above in Example. Three compounds were identified, one being compound 4 and two others having similar UV to compound 4. This sample was dissolved in methylene chloride and charged to a small silica column (60 ml) in 9:1, methylene chloride:methanol and 1 column volume of each of 3:1, 1:1 and methanol used for elution. Cuts 21–30 contained compound 6 (1.5 mg) and cuts 71–76 contained compound 7 (1.2 mg). Both compounds were characterized by $^1$H NMR and MS.

Scanning HR-EI data are indicated below.

| Found | Calculated | Formula | Assignment |
|---|---|---|---|
| Compound 6 | | | |
| 599.3538 | 599.3610 | C38H49NO5 | M+ |

1H NMR data was recorded in $CDCl_3$ or $CD_3OD$ on a 300 MHz Vairan spectrometer. Chemical shifts are indicated in ppm relative to TMS at zero ppm using the solvent peaks as internal standards.

Compound 6 (300 MHz): δ1.0(3H,s), 1.07(3H,s), 1.10 (3H,s), 1.30(3H,s), 1.32(3H,s), 1.33(3H,s), 1.40(3H,s), 1.87 (3H,s), 2.0(1H,m), 2.2(2H,m), 2.3(1H,m), 2.65(1H,m), 2.7 (1H,m), 2.8(1H,m), 2.9(1H,m), 3.1(1H, dd J=9.6, 15.6 Hz), 3.35(1H,m), 4.85(1H,dd J=10.2,16.8 Hz), 5.94(1H,d J=3 Hz), 6.83(1H,d J=8.4 Hz), 7.12(1H,s), 7.47(1H,s).

Compound 7 (300 MHz): δ0.95(3H,s), 1.0(3H,s), 1.1 (3H,d J=4 Hz), 1.3(3H,s), 1.31(3H,s), 1.32(3H,s), 1.33(3H, s), 1.35(3H,s), 1.7(2H,m), 2.15(1H,m), 2.25(1H,m), 2,4(1H, m), 2.6(1H,m), 2.7(1H,m), 2.8(1H,m), 5.90(1H,d J=3 Hz), 7.11(1H,s), 7.37(1H,s)

EXAMPLE 9

Purification and Characterization of Compound 8

3 Kg of a dried methanol eluent from an SP207 caputre column, from the fermentation of MF 6047 (ATCC 74380) was dissolved in methylene chloride/acetone and charged to a large silica funnel and eluted with 3:1, hexane-acetone followed with 1:1; acetone; 1:3, methanol-acetone; 1:1 (methanol-acetone); and methanol. Cuts of interest were combined (75 g), dried under vacuum and charged to a large Sephadex LH20 funnel to eliminate impurities batch wise. The cuts containing the compounds of interest were dried and charged to a large (4 liter) LH20 column. Cuts 27–36 contained the compound of interest (7.5 g) and was dried under vacuum, dissolved in methylene chloride and charged to a silica gel column in 7:3:0.1; methylene chloride-acetone-water, followed by 1:1:0.1; 1:3:0.1; acetone and methanol. Cuts 65–75 contained the new compound (440 mg). This material was fractionated on a small silica gel column (100 cc) in the 7:3:0.1 solvent above and cuts (37–42) contained the new peak as determined by TLC and HPLC. Next a prep TLC (9:1; methylene chloride:methanol; silica gel 60) followed by semi-prep HPLC was used for final purification of compound 8 (12 mg). This compound was characterized as an analog of compounds 1–3 by NMR and MS.

Critical high resolution data is indicated below:

| Found | Calculated | Formula | Assignment |
|---|---|---|---|
| Compound 8 | | | |
| — | — | $C_{43}H_{57}NO_5$ | |
| 649.4174 | 649.4131 | $C_{43}H_{55}NO_4$ | M – H$_2$O |

$^1$H and $^{13}$C NMR data $^{13}$C NMR data were recorded in CD$_3$OD at 100 MHz on a Varian Unity 400 MHz spectrometer at 25° C. Chemical shifts are in ppm relative TMS at zero ppm using the solvent peak at 49.0 ppm as internal standard.

Compound 8(100 MHz): 176.66, 153.57, 151.6, 142.74, 137.79, 136.97, 136.5, 132.48, 132.43, 131.63, 127.96, 127.0, 124.8, 123.71, 119.64, 119.19, 107.76, 77.9, 76.7, 75.7, 74.17, 60.83, 54.72, 50.34, 47.0, 45.73, 40.16, 33.89, 32.18, 30.37, 30.19, 28.28, 27.7, 27.1, 26.43, 25.93, 25.64, 23.17, 19.46, 18.29, 14.77, 13.93, 11.97.

The carbon count is in agreement with the molecular formula $C_{43}H_{55}NO_4$ derived from HR MS.

$^1$H NMR spectra was recorded in CD$_3$OD on a 400 MHz spectrometer. Chemical shifts are indicated in ppm relative to TMS at zero ppm using the solvent peak as an internal standard.

Compound 8 (400 MHz):δ1.00(3H,s), 1.04(3H,s), 1.05 (3H,s), 1.17(3H,s), 1.31(6H, s), 1.45(3H,s), 1.71(3H,s), 1.85 (3H,s), 1.92(3H,d J=1.2 Hz), 2.25(1H,dd J=10.5,12.9 Hz), 2.58(1H,dd J=6.6,13.2 Hz), 2.7(2H, dd J=3.0,4.5 Hz), 3.4 (1H,dd J=4.8,9.9 Hz), 3.78(1H,dd J=6.0,15.6 Hz), 3.91(1H, dd J=7.8,15.6 Hz), 5.02(1H,d J=4.8 Hz), 5.73(1H,d J=15.3 Hz), 5.91(1H,d J=3 Hz), 6.33(1H,dd J=11.1, 15.3 Hz), 7.04(1H,d J=11.1 Hz), 7.28(1H,s).

EXAMPLE 10

Purification and Characterization of Compounds 9, 10 and 11, methyl esters of Compound 12, 13 and 14, respectively)

A new mutant culture, MF 6206 (ATCC 74382), produced 3 new compounds as the major components. Upon purification of the compounds by HPLC using TFA as a buffer or even at neutral pH the compounds slowly decomposed. Therefore, a fermentation extract was dried and dissolved in 1:1 methanol-methylene chloride(10 cc). Trimethylsilyldiazomethane/hexane was added and the reaction was completed in 15 minutes as determined by HPLC. The extract was fractionated by prep TLC (silica gel) 95-5:methylene chloride-methanol. Cuts were evaluated by HPLC and NMR and determined to be compound 9 (methyl ester of 12) and compound 10 (methyl ester of 13). Not enough of compound 11 (methyl ester of 14) was isolated for structural determination, but is present by inference (cmpds 9 & 10 as well as 12, 13 & 14) and HPLC detection.

High resolution MS was determined on compound 9 and the molecular weights of compound 10 and the mixture of all three unesterified compounds (12,13 & 14 natural compounds) were determined by LC-MS. High resolution and mass spectral data is indicated below:

| Found | Calculated | Formula | Assignment |
|---|---|---|---|
| Compound 9 | | | |
| 679.4165 | 679.4236 | $C_{44}H_{57}NO_5$ | M+ |
| Compound 12 | | | |
| 665 | 665 | | Seen in mixture |
| Compound 13 | | | |
| 699 | 699 | | Seen in mixture |
| Compound 14 | | | |
| 681 | 681 | | Seen in mixture |

1H NMR data for compounds 9 & 10

1H NMR spectra were recorded in CD$_2$Cl$_2$ on a 400 MHZ spectrometer. Chemical shifts are indicated in ppm relative to TMS at zero ppm using the solvent peak as an internal standard.

Compound 9 (400 MHz):δ0.93(3H,s), 1.05(3H,s), 1.10 (6H,s), 1.27(3H,s), 1.29(3H,s), 1.32(3H,s), 1.43(3H,s), 1.96 (3H,d J=1.6 Hz), 2.2(1H,dd J=10.8,14.0 Hz), 2.65(1H,dd J=7.2,10.4 Hz), 2.65(1H,dd J=7.4,8.8 Hz), 2.75(1H,m), 3.4 (1H,dd J=4.8,10.8 Hz), 3.5(1H,d J=16.8 Hz), 3.75(3H,s, OCH$_3$), 4.05(1H,dd J=8.8,16.8 Hz), 4.7(1H,s), 4.82(1H,m), 4.95(1H,m), 5.25(1H,d J=6.8 Hz), 5.88(1H,d J=15.2 Hz), 5.95(1H,d J=2.8 Hz), 6.4(1H,dd J=11.2,15.2 Hz), 7.22(1H,d J=11.2 Hz), 7.27(1H,s)

Compound 10 (400 MHz):δ0.9(3H,s), 1.04(3H,s), 1.1 (3H,d J=10.8 Hz), 1.28(9H,s), 1.30(3H,s), 1.32(3H,s), 1.4 (3H,s), 2.2(1H,m), 2.65(1H,m), 2.8(1H,m), 3.5(1H,d J=16.4 Hz), 3.7(3H,s,OCH$_3$), 4.05(1H,dd J=6.8,13.6), 4.55(1H,m), 4.76(1H,s), 4.82(1H,m), 4.96(1H,d J=5.2), 5.25(1H,d J=6.8 Hz), 5.96(1H,d J=3.2 Hz), 7.27(1H,s)

Hydrolysis of Compound 9

To a solution of compound 9 (3 mg) in methanol-water (9:1, 1.5 mL) was added potassium carbonate (10 mg) and reaction was stirred at room temperature for 24 hrs. Lithium hydroxide (10 mg) was added and the reaction mixture was stirred at room temperature for additional 24 hrs. HPLC examination indicated formation of a polar product. After completion, the reaction was quenched with 10% aqueous citric acid (2 mL) and was extracted with ethyl acetate (50 mL). The organic layer was washed with water, dried over sodium sulfate and concentrated to give a product which was purified by reverse phase HPLC on a Whatman ODS-3 column (9.4×250 mm). The product was eluted with a 50 minute gradient of 60% aqueous acetonitrile to 70% acetonitrile both containing 0.1% trifluoroacetic acid at a flow rate of 4 mL per minutes. Lyophilization of the fractions eluting between 26–30 minutes gave pure compound 12 (2 mg) as a yellow powder, FAB-MS (m/z): 648 (M-$H_2O$+H).

EXAMPLE 11

Purification and Characterization of Compound 15 and Compound 16)

2.0 grams of fermentation methyl ethyl ketone extract (Culture MF 6087 (ATCC 74381)) was dried, dissolved in methanol and fractionated on a Sephadex LH20 column (1000 cc; methanol) and eluted with methanol. The cuts containing the new compound (1.6 g) with similar UV spectra to compound 1, was dissolved in methanol and charged to a Waters Symmetry semi-prep C-18 HPLC column and eluted with 65-35:acetonitrile-water with 0.1% TFA. Cuts 26–27 contained the new compound and when dried had a weight of 2.8 mg. Upon reevaluation of compound 15 by HPLC another component (16) was observed. The possible elimination of the hydroxyl group (dehydration) under acidic conditions may have occurred as seen before. This material containing 2 compounds was fractionated by silica gel TLC and the components separated. Compounds 15 (1 mg) and 16 (1.5 mg) were evaluated by HPLC, TLC and NMR and determined to be related to compounds 1–3.

High resolution FAB-MS data was obtained for compound 15 and HR-ESI data was obtained for compound 16.

| Found | Calculated | Formula | Assignment |
| --- | --- | --- | --- |
| Compound 15 | | | |
| 678.3827 | 678.3794 | C43H52NO6 | M + H |
| Compound 16 | | | |
| 660.3674 | 660.3689 | C43H50NO5 | M + H |

1H NMR spectra were recorded in $CDCl_3$ on a 400 MHz spectrometer. Chemical shifts are indicated in ppm relative to TMS at zero ppm using the solvent peak as an internal standard.

Compound 15 (400 MHz):δ0.99(3H,s), 1.17(3H,s), 1.28 (3H,s), 1.33(3H,s), 1.37(3H,s), 1.38(3H,s), 1.45(3H,s), 1.51 (3H,s), 1.99(3H,s), 2.2(4H,m), 2.38(1H,dd J=10.4,14 Hz), 2.53(1H, dt J=15.6 Hz), 2.7(1H,dq J=15.2 Hz), 2.83(1H,dd J=6.4,14 Hz), 2.91(1H,dd J=3.2,6.4 Hz), 2.92(1H,m), 3.2 (1H,m), 5.07(1H,br.s), 5.11(1H,s), 5.26(1H,s), 5.27(1H,d J=6.8 Hz), 6.08(1H,d J=15.6 Hz), 6.09(1H,d J=3.2 Hz), 6.37(1H,dd J=11.2,15.6 Hz), 7.32(1H,d J=11.2 Hz), 7.74 (1H,s)

Compound 16(400 MHz):δ0.99(3H,s), 1.28(3H,s), 1.33 (3H,s), 1.46(3H,s), 1.51(3H,s), 1.52(3H,s), 1.59(3H,s), 1.60 (3H,s), 1.99(3H,d J=0.8 Hz), 2.2(4H,m), 2.37(1H,dd J=10.4, 14 Hz), 2.53(1H,dt J=15.6 Hz), 2.70(1H,dq J=15.2 Hz), 2.81(1H,dd J=6.8,14 Hz), 2.9(1H,m), 5.02(1H,s), 5.04(1H, br.s), 5.11(1H,s), 6.1(1H,d J=15.2), 6.36(1H,dd J=11.2, 15.2), 6.8(1H,d J=1.6 Hz), 6.88(1H,d J=1.2 Hz), 7.35(1H,d J=11.6 Hz), 7.81(1H,s)

EXAMPLE 12

Purification and Characterization of Compound 17 and Compound 18

Two liters of a fermentation broth (MF 6222) was extracted with MEK in the usual manner and the dried weight of the extract was 4.2 grams. HPLC analysis of the extract using standard conditions, indicated compound 8 as the main component with two other major components at 8.1 and 14.7 minutes retention time with compound 8 at 9.7 minutes. The UV profiles were similar for all three peaks in the chromatogram. 40 mg of extract in methylene chloride was charged to a silica gel TLC plate (20×20, E-Merck) and eluted with 9:1; methylene chloride:methanol and fractions eluted with methanol and dried and weighed. Cut 3, corresponding to the peak at r.t. of 14.7 min., had a weight of 5 mg and cut 4, corresponding to a peak at r.t. of 8.1 minutes, had a weight of 3.8 mg. By HPLC evaluation of these cuts compound 17 (Cut 3) and compound 18 (Cut 4) were nearly pure. Samples were evaluated by MS and $^1$H NMR.

High resolution -ESI data was obtained for compound 18 and LC-MS data for compound 17 and is shown below:

| Found | Calculated | Formula | Assignment |
| --- | --- | --- | --- |
| Compound 17 | | — | |
| 683 | 683.4186 | C43H57NO6 | |
| Compound 18 | | | |
| — | — | C43H59NO7 | |
| 665.4055 | 665.4080 | C43H55NO5 | M − 2 × $H_2O$ |

$^1$H NMR

1H NMR data was recorded in CD2Cl2 at 400 Mhz on a Varian Unity 400 Mhz spectometer at 25° C. Chemical shiofts are in ppm relative TMS at zero ppm using the solvent peak as internal standard.

Compound 17 (400 MHz):δ1.0(3H,s), 1.07(3H,s), 1.13 (3H,s), 1.30(6H,s), 1.43(3Hs), 1.44 (3H,s), 1.50(3H,s), 1.71 (3H,s), 1.85(3H,s), 2.3(1H,m), 2.6(1H,m), 2.8(1H,m), 5.1 (1H,m),5.9(1H,s), 6.6(1H,m), 7.37(1H,s).

Compound 18(400 MHz):δ0.95(3H,s), 1.0(3H,s),1.03 (3H,s), 1.07(3H,s),1.13(3H,s),1.31 (6H,s),1.43(3H,s),1.58 (3H,s),1.74(3H,s),3.1(1H,m),5.03(1H,m), 5.94(1H,s),7.34 (1H,s).

EXAMPLE 13

General Method for the Mutation of Nodulisporium sp. using NTG

Method A

A 50-mL portion of Seed Medium SM1 in a non-baffled 250-mL Erlenmeyer flask was inoculated with 2 mL of a mycelial suspension of a Nodulisporium strain, and the resulting culture was incubated with shaking at 220 rpm for 3 days in darkness at 29° C. Portions (2 mL) of this seed culture were transferred into 2 fresh 50-mL portions of KF seed Medium, and the new cultures were shaken at 220 rpm at 29° C. Following incubation for 6 hours, NTG (N-methyl-N'-nitro-N-nitrosoguanidine, dissolved in methanol) was added to 1 of the cultures at a final concentration of 10 μg mutagen/mL, the remaining culture being the control. Both cultures were incubated with shaking at 220 rpm in darkness at 29° C. for an additional 42 hours. The mycelia in the entire 50-mL volume of the NTG-treated culture were fragmented in a VERTIS 45 homogenizer; the cells were chilled on ice and homogenized for 4 minutes. The entire suspension was then passed through 4 layers of sterile cheesecloth with large fragments being retained in the cloth and smaller fragments passing through. Following filtering, 25 mL of the suspension were transferred into sterile tubes and centrifuged at 1000 rpm for 10 minutes. The supernatant was collected and centrifuged further at 3000 rpm for 10 minutes. The supernatant was discarded, and the cell pellet was resuspended in 2 ml of sterile water. Serial dilutions in sterile water were plated on agar growth media containing cyclosporin at 5 μg/ml to restrict radial growth. The media used for plating were Potato Dextrose Agar [Difco] and YNB:cellobiose (Yeast Nitrogen Base without ammonium sulfate and amino acids [Difco], 2% cellobiose, 0.5% ammonium sulfate, 2% agar in 50 mM MES {2-[N-morpholino]ethanesulfonic acid} buffer, pH 6.0. The control culture was likewise homogenized, filtered, diluted, and plated. The plates were incubated at 25° C. Between 9 and 19 days incubation, survivors of the NTG treatment were picked and propagated on agar plates of the same medium. One of the survivors was MF6206.

Method B

Mycelia are harvested after 48 hrs of growth in supplemented YNB broth at 29° C. and 220 RPM by vacuum filtration onto sterile Mira cloth. The mycelial pad is resuspended in broth and homogenized for 2 minutes. A combination of low speed centrifugation and filtration is used to remove large mycelial pieces from the homogenized suspension and the remaining small mycelial fragments are pelleted by centrifugation and then resuspended in 50 ml of fresh broth and incubated at 29° C. and 220 RPM for 6 hrs. The fragments are then collected by vacuum filtration onto the surface of 0.2μ filter unit and resuspended in 10 ml water. NTG dissolved in methanol is then added to a final concentration of 400 μg/ml and the suspension incubated at 29° C. and 100 RPM. Aliquots are removed, washed with 50 mM TRIS-pH7. and resuspended in broth after 10, 20, 30, and 40 minutes exposure to NTG. These suspensions are serially diluted and plated on agar containing cyclosporin at 5 μg/ml to restrict growth and then incubated at 29° C. until colonies appear. MF6222 was obtained by this method.

Supplemented YNB medium has the following composition:

| Supplemented Yeast NItrogen Base (YNB) | | |
|---|---|---|
| NaNO₃ | 6 | g |
| H₂O | 900 | ml |

Sterilize by autoclaving.
Poststerile add: 100 ml of following 10X solution

| | | |
|---|---|---|
| Yeast Nitrogen Base | 1.7 | g |
| Yeast Extract | 1 | g |
| Peptone | 1 | g |
| Casamino Acids | 1 | g |
| H₂O | 100 | ml | filter sterilize and add to solution above plus
20 ml of filter sterilized 50% glucose

EXAMPLE 14

Characteristics of MF6047 (ATCC 74380)

MF6047 (ATCC 74380) is a mutant of Nodulisporium sp. (ATCC 74245, MF5954) produced by NTG mutagenesis of vegetative mycelium of this strain. The culture mat morphology and microscopic dimensions of MF6047 are essentially similar to those described in U.S. Pat. No. 5,399,582 (Mar. 21, 1995) except that MF6047 (ATCC 74380) produces a higher titer of compound 1 under the same conditions as ATCC 74245. In addition, the culture mat shows evidence of sectoring as different areas of the culture mat exhibit abnormal color patterns and textures.

EXAMPLE 15

Characteristics of MF6087 (ATCC 74381)

MF6087 (ATCC 74381) is a mutant of Nodulisporium sp. (ATCC 74245, MF5954) produced by NTG mutagenesis of vegetative mycelium of this strain. The culture mat morphology and microscopic dimensions of MF6087 are essentially similar to those described in U.S. Pat. No. 5,399,582 (Mar. 21, 1995) except that MF6087 (ATCC 74381) produces a higher titer of compound 1 under the same conditions as ATCC 74245.

EXAMPLE 16

Characteristics of MF6206 (ATCC 74382)

MF6206 (ATCC 74382) is a mutant of Nodulisporium sp. (ATCC 74245, MF5954) produced by sequential NTG mutagenesis of vegetative mycelium of this strain. MF6206 (ATCC 74382) exhibits significantly different culture mat morphology to that described in U.S. Pat. No. 5,399,582 (Mar. 21, 1995) for ATCC 74245. MF6206 (ATCC 74382) grows at a slower rate; under the same environmental conditions, on cornmeal agar, MF6206 grows 11 mm in 6 days, while ATCC 74245 grows 42 mm in 6 days. MF6206 produces no aerial mycelium on oatmeal agar. Also on oatmeal agar, MF6206 exhibits a pink (Onion-skin Pink, Light Vinaceous Cinnamon) colony color while ATCC 74245 is a yellow-brown (Mars Yellow, Raw Sienna) to light yellow brown (Light Orange Yellow, Antimony Yellow) colony color. In addition, MF6206 (ATCC 74382) does not produce conidiophores or conidia.

EXAMPLE 17

Characteristics of MF6222 (ATCC 74383)

MF6222 (ATCC 74383) is a mutant of Nodulisporium sp. (ATCC 74245, MF5954) produced by sequential NTG mutagenesis of vegetative mycelium of this strain. MF6222 (ATCC 74383) exhibits significantly different culture mat morphology to those described in U.S. Pat. No. 5,399,582 (Mar. 21, 1995) as that of ATCC 74245. MF6222 (ATCC 74383) grows at a slower rate; on cornmeal agar, MF6222 grows 6 mm in 6 days, while ATCC 74245 grows 42 mm in 6 days. MF6222 produces no aerial mycelium on oatmeal agar. Also on oatmeal agar, and like MF6206, MF6222 exhibits a pink (Onion-skin Pink, Light Vinaceous Cinnamon) colony color while ATCC 74245 exhibits a yellow-brown (Mars Yellow, Raw Sienna) to light yellow brown (Light Orange Yellow, Antimony Yellow) colony color. In addition, MF6222 (ATCC 74383) does not produce conidiophores or conidia.

What is claimed is:

1. A biologically pure culture of a Nodulisporium sp. having the identifying characteristics of MF6047 (ATCC 74380), MF6087 (ATCC 74381), MF6206 (ATCC 74382) or MF6222 (ATCC74382), and produces a compound selected from the group consisting of:

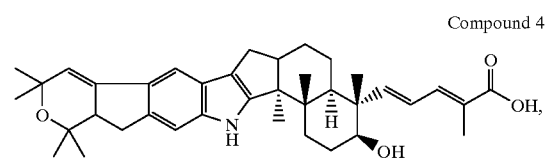

Compound 4

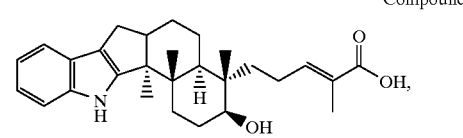

Compound 5

Compound 6:
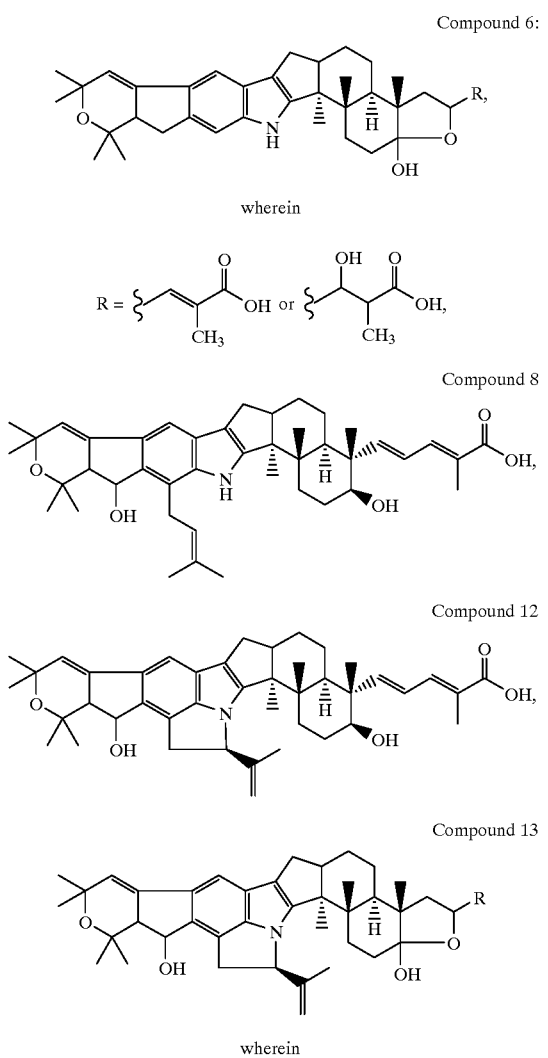
wherein
Compound 8
Compound 12
Compound 13
wherein
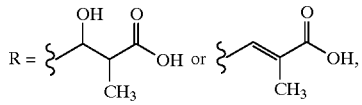
Compound 15
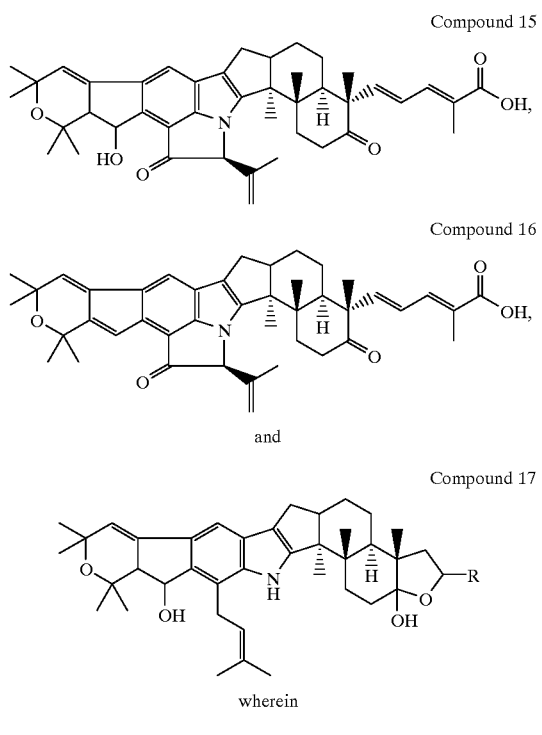
Compound 16
and
Compound 17
wherein
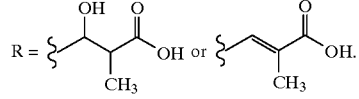
* * * * *